United States Patent [19]

Nozawa et al.

[11] Patent Number: 5,171,821
[45] Date of Patent: Dec. 15, 1992

[54] PROCESS FOR PRODUCING A PHENOLATE AND PROCESS FOR PRODUCING AN AROMATIC POLYETHER KETONE EMPLOYING IT

[75] Inventors: Seiichi Nozawa, Yamato; Hiroshi Noguchi, Yokohama; Fumitoshi Sakaguchi, Machida; Yuko Mihara, Tokyo, all of Japan

[73] Assignee: Mitsubishi Kasei Corporation, Tokyo, Japan

[21] Appl. No.: 359,637

[22] Filed: May 31, 1989

[30] Foreign Application Priority Data

May 31, 1988 [JP] Japan .................. 63-131583
Jun. 7, 1988 [JP] Japan .................. 63-138351

[51] Int. Cl.$^5$ .................. C08G 2/00; C08G 8/02; C08G 14/04; C08G 65/38
[52] U.S. Cl. .................. 528/125; 528/126; 528/172; 528/174; 528/212; 528/214; 528/217; 528/220; 528/222; 528/223
[58] Field of Search .............. 528/125, 126, 172, 174, 528/222, 223

[56] References Cited

U.S. PATENT DOCUMENTS

| | | | |
|---|---|---|---|
| 4,307,222 | 12/1981 | Schwab et al. | 528/126 |
| 4,320,224 | 3/1982 | Rose et al. | 528/126 |
| 4,757,126 | 7/1988 | Fukawa et al. | 528/125 |
| 4,774,311 | 9/1988 | Kelsey | 528/126 |
| 4,774,314 | 9/1988 | Winslow et al. | 528/126 |
| 4,835,242 | 5/1989 | Eggersdorfer et al. | 528/126 |
| 4,837,296 | 6/1989 | Heinz et al. | 528/126 |
| 4,952,665 | 8/1990 | Ebata et al. | 528/126 |
| 4,954,604 | 9/1990 | Genz et al. | 528/126 |

FOREIGN PATENT DOCUMENTS

63-27448 2/1988 Japan .

*Primary Examiner*—John Kight, III
*Assistant Examiner*—P. Hampton-Hightower
*Attorney, Agent, or Firm*—Oblon, Spivak, McClelland, Maier & Neustadt

[57] ABSTRACT

A process for preparing a metal phenolate of the formula II:

$$Cl-Ar_1COAr_2OM \qquad (II)$$

wherein each of $Ar_1$ and $Ar_2$ which may be the same or different is a bivalent group of the formula:

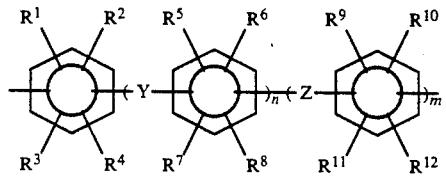

wherein each of $R^1$ and $R^{12}$ is a hydrogen atom, a halogen atom, an alkoxy group, a phenoxy group, an alkyl group, a cycloalkyl group, a phenyl group, an aralkyl group, an acyl group, a nitrile group, a nitro group or an acyloxy group, each of Y and Z is an oxygen atom or a ketone group, and each of n and m is an integer of from 0 to 4, and M is an alkali metal, which comprises reacting a phenol compound of the formula I:

$$Cl-Ar_1COAr_2OH \qquad (I)$$

wherein $Ar_1$ and $Ar_2$ are as defined above, with an alkali metal compound in the presence of water, and then removing water, characterized in that water is azeotropically distilled off together with an organic solvent capable of forming an azeotropic mixture with water.

6 Claims, No Drawings

PROCESS FOR PRODUCING A PHENOLATE AND PROCESS FOR PRODUCING AN AROMATIC POLYETHER KETONE EMPLOYING IT

The present invention relates to a process for preparing a metal phenolate of a high purity and a process for producing an aromatic polyether ketone having a high degree of polymerization in good yield by using the metal phenolate.

A phenolate of the formula II:

$$Cl-Ar_1COAr_2OM \qquad (II)$$

wherein each of $Ar_1$ and $Ar_2$ which may be the same or different is a bivalent group of the formula:

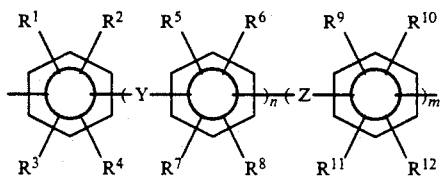

wherein each of $R^1$ to $R^{12}$ is a hydrogen atom, a halogen atom, an alkoxy group, a phenoxy group, an alkyl group, a cycloalkyl group, a phenyl group, an aralkyl group, an acyl group, a nitrile group, a nitro group or an acyloxy group, each of Y and Z is an oxygen atom or a ketone group, and each of n and m is an integer of from 0 to 4, and, M is an alkali metal, is a prospective intermediate useful for preparation of polyether ketones. However, a compound of the formula I:

$$Cl-Ar_1COAr_2OH \qquad (I)$$

wherein $Ar_1$ and $Ar_2$ are as defined above, used as the starting material, has a chlorine atom and a free hydroxyl group in its molecule. Accordingly, when such compound is reacted with an alkali metal compound to obtain an alkali metal phenolate, side reactions such as hydrolysis of the chlorine atom and low polymerization, are likely to take place, and water tends to remain, whereby it has been difficult to obtain an alkali metal phenolate in high purity with a low water content without substantially containing impurities.

Further, the aromatic polyether ketone has low water absorptivity and is excellent in the mechanical and electrical properties and in the chemical resistance. It is therefore used as an engineering plastic, for example, in the application to precision parts such as electronic materials. For its production, a method by a ketone synthesis route and a method by an ether synthesis route have been known.

For the former ketone synthesis route, it is well known to polymerize an aromatic carboxylic acid halide in an aprotic organic solvent in the presence of aluminum chloride, or to polymerize an aromatic carboxylic acid halide in a hydrogen fluoride solvent in the presence of boron trifluoride. However, in these methods, a Lewis acid such as aluminum chloride or boron trifluoride is required to be used in an at least equimolar amount to the substrate, thus leading to problems in handling or in connection with corrosion of the equipments.

On the other hand, for the ether synthesis route, it is known to polymerize a 4,4'-difluorobenzophenone with aromatic dihydroxy compound under heating in the presence of an alkali metal carbonate. However, in such a method, it is usually difficult to obtain a polymer having a high degree of polymerization, since the hydrolysis of the halogen tends to simultaneously proceed during the preparation of the alkali metal salt of phenolate and during the polymerization if the dihalogenobenzophenone is other than fluoride.

The present inventors have conducted extensive researches with an aim to solve the above-mentioned problems and to obtain a metal phenolate of a high purity containing no substantial impurities in good yield. As a result, they have found that the above-mentioned side reactions are caused by the high temperature treatment for the removal of water, and have conducted a further research on the basis of this discovery. As a result, it has been found possible to readily obtain an aromatic polyether ketone having a high degree of polymerization from an inexpensive chloride as opposed to the conventional expensive fluoride by reacting the compound of the formula I with an alkali metal compound in the presence of water to obtain a metal phenolate of the formula II, azeotropically distilling off water in the system with an organic solvent capable of forming an azeotropic mixture with water to obtain a phenolate, and polymerizing the phenolate in an organic solvent. The present invention has been accomplished on the basis of this discovery.

The present invention provides a process for preparing a metal phenolate of the formula II:

$$Cl-Ar_1COAr_2OM \qquad (II)$$

wherein each of $Ar_1$ and $Ar_2$ which may be the same or different is a bivalent group of the formula:

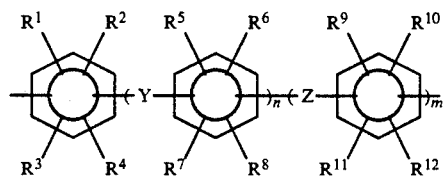

wherein each of $R^1$ to $R^{12}$ is a hydrogen atom, a halogen atom, an alkoxy group, a phenoxy group, an alkyl group, a cycloalkyl group, a phenyl group, an aralkyl group, an acyl group, a nitrile group, a nitro group or an acyloxy group, each of Y and Z is an oxygen atom or a ketone group, and each of n and m is an integer of from 0 to 4, and M is an alkali metal, which comprises reacting a phenol compound of the formula I:

$$Cl-Ar_1COAr_2OH \qquad (I)$$

wherein $Ar_1$ and $Ar_2$ are as defined above, with an alkali compound in the presence of water, and then removing water, characterized in that water is azeotropically distilled off together with an organic solvent capable of forming an azeotropic mixture with water. The present invention also provides a process for preparing an aromatic polyether ketone, which comprises a step of preparing a phenolate by the above-mentioned process and a step of thermally polymerizing the phenolate in a polymerization solvent at a temperature of from 250° to 400° C.

Now, the present invention will be described in detail with reference to the preferred embodiments.

In the present invention, firstly the compound of the formula I is reacted with an aqueous solution of an alkali compound to obtain a phenolate, and then water is removed to obtain the metal phenolate of the formula II. The compound of the formula I to be used as the starting material, includes, for example, 4-chloro-4'-hydroxybenzophenone, 4-(4-chlorophenoxy)-4'-hydroxybenzophenone, 4-(4-chlorophenoxy)-4'-(4-hydroxyphenoxy)benzophenone, 1-(4-chlorophenyl)-4-(4'-hydroxyphenoxy)benzene, 1-(4-chlorobenzoyl)-4-(4'-hydroxybenzoyl)benzene and 1 (3-chlorophenoxy)-4-(4'-hydroxybenzoyl)benzene, 1-(4-chlorobenzoyl)-4-(4'-hydroxybenzoyl)benzene. Among them, the most preferred is 4-chloro-4'-hydroxybenzophenone.

On the other hand, as the alkali compound to be reacted with the compound of the formula I, any compound which shows alkalinity when dissolved in water, may be employed. Specifically, potassium hydroxide, potassium carbonate, potassium hydrogen carbonate, potassium phosphate, potassium acetate, sodium hydroxide, sodium carbonate, sodium hydrogen carbonate, sodium borate or lithium hydroxide may, for example, be mentioned. Among them potassium hydroxide is preferred.

The alkali compound is used in an amount of from 0.950 to 1.015 mol, preferably from 0.97 to 1.005 mol, per mol of the compound of the formula I. If the amount is less than 0.950, the metal phenolate of the formula II can not be obtained in high purity unless the unreacted compound of the formula I is removed. If the amount exceed 1.015, water tends to remain in the metal phenolate, and when the product is heated at a high temperature, the hydrolysis of chlorine is promoted substantially, whereby the hydrolysate serves as a polymerization terminator, and preparation of a polymer will be difficult.

For the reaction, it is preferred that the compound of the formula I is preliminarily dissolved in the aqueous solution of an alkali compound.

The process of the present invention comprises reacting the compound of the formula I with an alkali compound in the presence of water to form a phenolate, and then removing the water to obtain a phenolate, wherein for the removal of water, an organic solvent capable of forming an azeotropic mixture with water (hereinafter referred to simply as an azeotropic solvent) is used to azeotropically distilling off water with the azeotropic solvent, whereby a solid metal phenolate is obtainable.

Various types of solvents may be used as the azeotropic solvent. However, it is preferred to use a solvent having an azeotropic temperature of not higher than 200° C., more preferably not higher than 150° C., to obtain a phenolate of a high purity while suppressing side reactions. Specifically, benzene, heptane, xylene, chlorobenzene, dichlorobenzene, chloroform, acetonitrile, 1,2-dichloroethane, ethanol, dimethylsulfoxide, cyclohexane, isopropyl alcohol, 1,3-dioxane and methyl ethyl ketone may be mentioned. However, xylene is particularly preferred, since the operation will thereby be easy.

In the above embodiment, the azeotropic solvent was added after the conversion to the phenolate. However, the azeotropic solvent may be incorporated at the initial state when the compound of the formula I is dissolved in the aqueous solution of an alkali compound. Further, the azeotropic solvent may be used in combination with the above-mentioned high boiling point solvent.

The distillation of the azeotropic mixture of water and the azeotropic solvent can be conducted under atmospheric pressure, under reduced pressure or under elevated pressure. The azeotropic solvent may be recovered from the azeotropic mixture and reused.

The mixing ratio of such an azeotropic solvent and water can not generally be defined, since it varies depending upon the azeotropic composition. However, it is preferred to employ the azeotropic solvent in an excess amount beyond the minimum amount required for removing all the water in the reaction system in the form of the azeotropic mixture. When the metal phenolate is to be isolated, the excess azeotropic solvent is distilled off under atmospheric pressure or under reduced pressure to obtain the metal phenolate in a powder form.

The metal phenolate of the formula II thus obtained by the process of the present invention, may then be polymerized in an organic solvent having a higher boiling point than the azeotropic solvent to obtain a polyether ketone. In such a case, a high boiling point solvent for polymerization may be used in combination with the above-mentioned azeotropic solvent. In this case, after the formation of the phenolate, water in the system is azeotropically distilled off together with the azeotropic solvent to obtain a high boiling point solvent solution or slurry of the metal phenolate, which is continuously be subjected to polymerization treatment. However, the water content can be made smaller by preparing the metal phenolate without incorporating such a solvent.

As the high boiling point solvent, diphenylsulfone, benzophenone, xanthene, diphenylether, dimethylaminoimidazolidinone, triethylene glycol dibutyl ether, hexamethylphosphonic acid amide and diphenylsulfoxide may, for example, be mentioned. Among them, diphenylsulfone is most preferred. These solvents may be used in combination.

Such a high boiling point organic solvent for polymerization may be mixed with a preliminarily prepared metal phenolate, followed by polymerization. In such a case, the solvent for polymerization is most preferably dehydrated before use.

Further, the fact that the halogen atom in the phenolate of the formula II is not hydrolyzed, can be confirmed by a GC method whereby the diphenol compound is trimethylsilylated and the presence or absence of the trimethylsilylated product is examined.

As the conditions for the GC method, the quantitative analysis of the trimethylsilylated product of the compound of the formula I was conducted at the inlet temperature of 250° C. and a column temperature of 200° C. by using a 2 m column of SE-30.5%, manufactured by Gaschro Kogyo K.K. Further, the quantitative analysis of the trimethylsilylated product of the diphenol compound was conducted at an inlet temperature of 250° C. with the column temperature being raised from 80° C. to 230° C. at a rate of 5° C./min. by using 1 m column of XE-60.25 manufactured by Gaschro Kogyo K.K.

The method for quantitative analysis of the water content in the metal phenolate will be described in Examples.

Water in the polymerization system adversely affects the degree of polymerization of the polymer. As a method for reducing water, there may be mentioned a method wherein after heating at a temperature of from 250° to 290° C. for from 0.5 to 4 hours, a step of removing water is again introduced, other than the above-mentioned method wherein the amount of alkali used is controlled. Such removal of water may be conducted by a method of again azeotropically distilling it with an azeotropic solvent or by a method of using a reagent reactive with water and capable of removing water, such as a Grignard reagent, diborane, an organoaluminum, phosphorus pentoxide or an organozinc compound. However, the method of removal of water is not restricted to such specific methods.

The polymerization is conducted usually at a temperature of from 200° to 400° C., preferably from 250° to 380° C., more preferably from 270° to 370° C., at a polymer concentration of from 1 to 50% by weight, preferably from 5 to 45% by weight. The polymerization may be conducted under an elevated pressure. The reaction time varies depending upon the polymerization temperature, but it is usually from 0.5 to 36 hours, preferably from 1.5 to 24 hours.

Now, the present invention will be described in further detail with reference to Examples. However, it should be understood that the present invention is by no means restricted to such specific Examples.

EXAMPLE 1

4-chloro-4'-hydroxybenzophenone/KOH=1/1 (molar ratio)

Into a reactor equipped with a stirrer, a nitrogen inlet, a thermocouple and a distillation device, 21.75 g (93.5 mmol) of 4-chloro-4'-hydroxybenzophenone and 93.5 mmol of 2N potassium hydroxide were charged, and the mixture was stirred at room temperature for 30 minutes while supplying dry nitrogen at a flow rate of 400 ml/min for conversion to phenolate. To a transparent yellow reaction solution thereby obtained, 140 ml of xylene was added, and azeotropic distillation was conducted over a period of 1.5 hours to distill off water and xylene. Heating was continued for further 30 minutes to remove the remaining xylene and a small amount of the remaining water, and the reaction was stopped when the internal temperature rose to 280° C. Thus, yellow powder of potassium salt of 4-chloro-4'-hydroxybenzophenone was obtained. This powder was accurately weighed in a dry box and put in Aquamicron AKS (Karl Fisher reagent, manufactured by Mitsubishi Kasei Corporation), and the water content was analyzed by means of a water content measuring apparatus CA-0.5, manufactured by Mitsubishi Kasei Corporation. As a result, the water content was 123 ppm. Namely, the water content was 0.19 mol % relative to 4-chloro-4'-hydroxybenzophenone. By the gas chromatography, low hydrolysis of the starting material (4-chloro-4'-hydroxybenzophenone) was detected in the potassium salt thus obtained.

EXAMPLES 2 to 4 and COMPARATIVE EXAMPLE 1

Each experiment was conducted in the same manner as in Example 1 except that the amount of 4-chloro-4'-hydroxybenzophenone was changed to 93.5 mol, and the amount of KOH was changed as shown below. The results are shown in Table 1.

TABLE 1

| KOH/4-chloro-4'-hydroxy-benzophenone (mol ratio) | Water content | |
|---|---|---|
| | ppm | mol %* |
| Example 2  0.99 | 71 | 0.11 |

TABLE 1-continued

| KOH/4-chloro-4'-hydroxy-benzophenone (mol ratio) | Water content | |
|---|---|---|
| | ppm | mol %* |
| Example 3  0.98 | 60 | 0.09 |
| Example 4  1.01 | 950 | 1.47 |
| Comparative Example 1  1.021 | 2275 | 3.52 |

*relative to 4-chloro-4'-hydroxybenzophenone

EXAMPLE 5

Into a reactor equipped with a stirrer, a nitrogen inlet, a thermocouple and a distillation device, 21.75 g (93.5 mmol) of 4-chloro-4'-hydroxybenzophenone and 93.5 mmol of 2N potassium hydroxide were charged, and the mixture was stirred at room temperature for 30 minutes while introducing dry nitrogen at a flow rate of 400 ml/min for conversion to phenolate. To a transparent yellow reaction solution thus obtained, 140 ml of xylene was added, and azeotropic distillation was conducted over a period of 1.5 hours to distill off water and xylene. Heating was continued for further 30 minutes to remove the remaining xylene and a small amount of the remaining water, and the reaction was stopped when the internal temperature rose to 280° C. Thus, yellow powder of potassium salt of 4-chloro-4'-hydroxybenzophenone was obtained. Then, to 21.31 g of the potassium salt of 4-hydroxybenzophenone, 47.08 g of diphenylsulfone preliminarily dehydrated by molecular sieve to a water content of 41 ppm, was mixed, and the mixture was stirred under a nitrogen stream and reacted at 280° C. for two hours and at a 320° C. for further 10 hours. The water content in the potassium salt of 4-chloro-4'-hydroxybenozophenone used for polymerization was 125 ppm, which corresponds to 0.19 mol relative to the potassium salt of 4-chloro-4'-hydroxybenzophenone.

For the post treatment of the polymer, the reaction mixture was cooled, pulverized and washed by refluxing with acetone three times each for 20 minutes to remove diphenylsulfone, then washed twice with hot water and vacuum-dried at 120° C. for 12 hours. The logarithmic viscosity number $\eta_{inh}$ of the polymer was 0.88 dl/g. The logarithmic viscosity number was measured in concentrated sulfuric acid (specific gravity: 1.84) at a temperature of 30° C. at a polymer concentration of 1.0 g/dl. The water contents in the potassium salt of 4-chloro-4'-hydroxybeozophenone and in diphenylsulfone were measured by accurately weighing the respective powders in a dry box and putting them in Aquamicron AKS (Karl Fisher reagent, manufactured by Mitsubishi Kasei Corporation) and measuring the water contents by means of the water content measuring apparatus CA-05 manufactured by Mitsubishi Kasei Corporation.

The dehydration of diphenylsulfone was conducted by adding molecular sieve 4A (preliminarily prepared by heating under vacuum at 320° C. for 8 hours) and heating at 140° C. for 6 hours.

The dried polymer was melt-extruded by a flow tester (CFT-500A, manufactured by Shimadzu Corporation) at 400° C. to obtain a strand. The strand thus obtained was extremely strong.

EXAMPLE 6

The reaction was conducted under the same condition as in Example 5 except that the reaction time at 320° C was changed to 4 hours. In this case, the logarithmic viscosity number $\eta_{inh}$ of the obtained polymer was 0.68 dl/g.

The dried polymer was subjected to Soxhlet extraction in water and acetone, and impurities were extracted with acetone and water and removed. The polymer was melted at 400° C. and maintained at 400° C. for 60 minutes. The polymer thus obtained was dissolved in sulfuric acid, and the viscosity was measured in the same manner as in Example 5, whereby no gelation took place, and the logarithmic viscosity number $\eta_{inh}$ was 0.69 dl/g. The dried polymer was melt-extruded by a flow tester (CFT500A, manufactured by Shimadzu Corporation) at 400° C. to obtain a strand. The strand thus obtained was strong.

The melting point (Tm), the crystallization temperature (Tc), the heat of fusion ($\Delta$Hm) and the heat of crystallization ($\Delta$Hc) were measured by DSC (DSC-20 manufactured by Seiko Denshi). The results were as follows: Tm=376.7° C., Tc=337.3° C., $\Delta$Hm=40.2 mJ/mg, and $\Delta$Hc=−43.7 mJ/mg.

EXAMPLE 7

Into a reactor equipped with a stirrer, a nitrogen inlet, a thermocouple and a distillation device, 21.75 g of 4-chloro-4'-hydroxybenzophenone and 93.5 mmol of 2N potassium hydroxide were charged, and the mixture was stirred at room temperature for 30 minutes while supplying dry nitrogen at a flow rate of 20 ml/min for conversion to phenolate. To the transparent yellow reaction solution thus obtained, 140 ml of xylene and 50 g of diphenylsulfone were added, and azeotropic distillation was conducted over a period of 1.5 hours to distill off water and xylene. Further, heating was continued for one hour to remove the remaining xylene and a small amount of the remaining water until the internal temperature rose to 280° C. After heating at 280° C. for two hours, the reaction mixture was cooled to 160° C., 140 ml of xylene was added thereto, and azeotropic distillation was again conducted to remove the xylene and a very small amount of the remaining water. Then, the temperature was raised to 320° C., and polymerization was conducted for 4 hours. After the polymerization, the reaction mixture was cooled. Then, in order to measure the water content in the reaction mixture, the reaction mixture was accurately weighed in a dry box and put in a heating furnace of a water content evaporating apparatus VA-21 manufactured by Mitsubishi Kasei Corporation, and the heating furnace was heated to 180° C. The water content carried by nitrogen was introduced to a titration cell containing Aquamicron AKS (Karl Fisher reagent, manufactured by Mitsubishi Kasei Corporation), and titration was conducted by means of a water content measuring apparatus CA-05, manufactured by Mitsubishi Kasei Corporation to determine the water content. The measured value was 0.55 mol % relative to the charged starting material 4-chloro-4'-hydroxybenzophenone.

For the post treatment of the polymer, the reaction mixture was pulverized, and the powder was washed by refluxing with acetone three times each for 20 minutes to remove diphenylsulfone, then washed twice with hot water and vacuum-dried at 120° C. for 12 hours. The polymer had a logarithmic viscosity number $\eta_{inh}$ of 0.57 dl/g. This logarithmic viscosity number was measured in concentrated sulfuric acid (specific gravity: 1.84) at a temperature of 30° C. at a polymer concentration of 1.0 g/dl.

EXAMPLE 8

The experiment was conducted in the same manner as in Example 7 up to cooling to 160° C. after heating at 280° C. for two hours. The starting material 4-chloro-4'-hydroxybeozophenone used was the same as in Example 7.

After cooling to 160° C., 5.62 mmol of triisobutylaluminum diluted with 20 ml of xylene was added to the product. Then, the temperature was raised to 320° C., and the reaction was conducted at 320° C. for 4 hours. The reaction mixture was cooled.and sampled, and the water content was measured in the same manner as in Example 7 and found to be 0.22 mol % relative to the charged 4-chloro-4'-hydroxybenzophenone. The reaction mixture was post-treated in the same manner as in Example 7. The logarithmic viscosity number ($\eta_{inh}$) of the polymer thus obtained was 0.69 dl/g.

EXAMPLE 9

The experiment was conducted in the same manner as in Example 7 except that no removal of water at 160° C. was conducted after heating at 280° C. for two hours, and the reaction was further conducted at 320° C. for 4 hours. 4-Chloro-4'-hydroxybenzophenone used in this Example was the same as used in Example 7. The water content was 2.23 mol % relative to the charged 4-chloro-4'-hydroxybenzophenone. After the post treatment conducted in the same manner as in Example 7, the logarithmic viscosity number $\eta_{inh}$ of the polymer was 0.45 dl/g.

EXAMPLE 10

Into a reactor equipped with a stirrer, a nitrogen inlet, a thermocouple and an azeotropic distillation device, 21.75 g (93.5 mmol) of 4-chloro-4'-hydroxybenzophenone, 52.5 g (potassium hydroxide: 93.5 mmol) of an aqueous potassium hydroxide solution having a concentration of 10% by weight were charged, and the mixture was stirred at room temperature for 30 minutes while supplying dry nitrogen at a flow rate of 200 ml/min, for conversion to phenolate.

To the transparent yellow reaction solution thereby obtained, 140 ml of xylene and 50 g of diphenylsulfone were added, and the mixture was heated at 100° C. for 1.5 hours to remove water as a azeotropic mixture with xylene. Then, the internal temperature was raised from 100° C. to 250° C. over a period of one hour, whereby excess xylene was distilled off. The reaction mixture was cooled to room temperature to obtain a brown solid product. The conversion to phenolate of this product was 99.75% as measured by a DC method. No biphenyl compound (by-product due to the hydrolysis of the chlorine atom) was detected.

EXAMPLE 11

Into a reactor equipped with a stirrer, a nitrogen inlet, a thermocouple and an azeotropic distillation device, 21.75 g (93.5 mmol) of 4-chloro-4'-hydroxybenzophenone and 52.5 g of an aqueous potassium hydroxide solution having a concentration of 10% by weight (potassium hydroxide: 93.5 mmol), were charged, and the mixture was stirred at room temperature for 30 minutes while supplying dry nitrogen at a flow rate of 200 ml/min, to conduct the reaction for conversion to phenolate. To the transparent yellow reaction solution thus obtained, 140 ml of xylene and 50 g of diphenylsulfone were added. The mixture was heated at 100° C. for two hours to distill off water as an azeotropic mixture with xylene. A part of the residual solution was sampled and cooled to obtain a phenolate, and the phenolate conversion was 99.75% as measured by the above-mentioned GC method. No biphenol (by product due to the hydrolysis of the chlorine atom) was detected.

The residual solution after distilling off water as an azeotropic mixture with xylene, was heated under atmospheric pressure (760 mmHg), and the internal temperature was raised to 250° C. over a period of one hour, whereby excess xylene was distilled off. Then, the temperature was further raised to 280° C., and the polymerization reaction was conducted under stirring for 12 hours. After completion of the polymerization reaction, the reaction mixture was cooled to room temperature, and a yellow brown solid product thus obtained was collected by filtration, pulverized and sieved with a screen having a mesh size of 1.0 mm to obtain fine powder. This powder was refluxed with acetone three times each for 20 minutes to remove diphenylsulfone, and then washed with hot water. Then, the product was dried in a vacuum drier at 120° C. under a pressure of 1 Torr for 12 hours to obtain a polyether ketone as creamy white powder. The yield of the polymer was substantially 100%, and the logarithmic viscosity number $\eta_{inh}$ was 0.50 dl/g.

The logarithmic viscosity number is the value measured in concentrated sulfuric acid (specific gravity: 1.84) at a temperature of 30° C. at a polymer concentration of 1.0 g/dl. The logarithmic viscosity number of polymers obtained by the conventional methods is from 0.2 to 0.3 dl/g., This indicates that the polymer obtained by this Example has a high degree of polymerization.

What is claimed is:

1. A process for producing an aromatic polyether ketone, comprising the steps:
  (a) preparing a metal phenolate of the formula II:

wherein each of $Ar_1$ and $Ar_2$ which may be the same or different is a bivalent group of the formula:

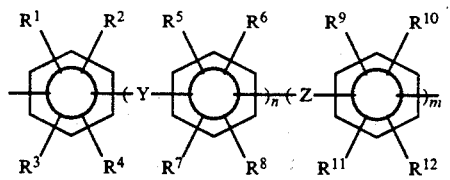

wherein each of $R^1$ to $R^{12}$ is a hydrogen atom, a halogen atom, an alkoxy group, a phenoxy group, an alkyl group, a cycloalkyl group, a phenyl group, an aralkyl group, an acyl group, a nitrile group, a nitro group or an acyloxy group, each of Y and Z is an oxygen atom or a ketone group, and each of n and m is an integer of from 0 to 4, and M is an alkali metal, which comprises reacting a phenol compound of the formula I:

wherein $Ar_1$ and $Ar_2$ are as defined above, with an alkali metal compound in the presence of water, and then removing water, characterized in that water is azeotropically distilled off together with an organic solvent capable of forming an azeotropic mixture with water; and
  (b) thermally polymerizing the phenolate in a polymerization solvent at a temperature of from 250° to 400° C.

2. A process for producing an aromatic polyether ketone, comprising the steps:
  (a) preparing a metal phenolate of the formula II:

Cl—Ar₁COAr₂OM    (II)

wherein each of $Ar_1$ and $Ar_2$ which may be the same or different is a bivalent group of the formula:

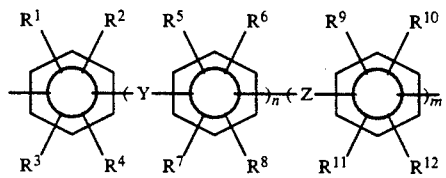

wherein each of $R^1$ to $R^{12}$ is a hydrogen atom, a halogen atom, an alkoxy group, a phenoxy group, an alkyl group, a cycloalkyl group, a phenyl group, an aralkyl group, an acyl group, a nitrile group, a nitro group or an acyloxy group, each of Y and Z is an oxygen atom or a ketone group, and each of n and m is an integer of from 0 to 4, and M is an alkali metal, which comprises reacting a phenol compound of the formula I:

wherein $Ar_1$ and $Ar_2$ are as defined above, with an alkali metal compound in the presence of water, and then removing water, characterized in that water is azeotropically distilled off together with an organic solvent capable of forming an azeotropic mixture with water; and
  (b) mixing said metal phenolate with a preliminarily dehydrated polymerization solvent; and
  (c) polymerizing said metal phenolate at a temperature of from 250° to 400° C.

3. A process for producing an aromatic polyether ketone which comprises a step of heating a metal phenolate in an organic solvent at a temperature of from 250° to 290° C. for from 0.5 to 4 hours, a step of removing water therefrom, and a step of further polymerizing it at a temperature of from 280° to 360° C.

4. The process according to claim 1, wherein the polymerization solvent is an aromatic sulfone compound.

5. The process according to claim 2, wherein the polymerization solvent is an aromatic sulfone compound.

6. The process according to claim 3, wherein the polymerization solvent is an aromatic sulfone compound.

* * * * *